US012752082B2

(12) United States Patent
Leuthardt et al.

(10) Patent No.: US 12,752,082 B2
(45) Date of Patent: Oct. 6, 2026

(54) VARIABLE STIFFNESS CATHETER AND METHODS THEREOF

(71) Applicant: Washington University, St. Louis, MO (US)

(72) Inventors: Eric Leuthardt, St. Louis, MO (US); Guy Genin, St. Louis, MO (US); Mohamed Zayed, St. Louis, MO (US); Daniel Hafez, St. Louis, MO (US); Chase Hartquist, St. Louis, MO (US); Halle Lowe, St. Louis, MO (US); Vinay Chandrasekaran, St. Louis, MO (US); Joshua Osbun, St. Louis, MO (US)

(73) Assignee: Washington University, St. Louis, MO (US)

( * ) Notice: Subject to any disclaimer, the term of this patent is extended or adjusted under 35 U.S.C. 154(b) by 901 days.

(21) Appl. No.: 17/794,790

(22) PCT Filed: Jan. 25, 2021

(86) PCT No.: PCT/US2021/014895
§ 371 (c)(1),
(2) Date: Jul. 22, 2022

(87) PCT Pub. No.: WO2021/151070
PCT Pub. Date: Jul. 29, 2021

(65) Prior Publication Data

US 2023/0070264 A1 Mar. 9, 2023

Related U.S. Application Data

(60) Provisional application No. 62/965,525, filed on Jan. 24, 2020.

(51) Int. Cl.
*A61M 25/01* (2006.01)
*A61M 25/00* (2006.01)

(52) U.S. Cl.
CPC .... *A61M 25/0138* (2013.01); *A61M 25/0045* (2013.01); *A61M 25/0054* (2013.01);
(Continued)

(58) Field of Classification Search
CPC .......... A61M 25/0138; A61M 25/0045; A61M 25/0155; A61M 2025/0025;
(Continued)

(56) References Cited

U.S. PATENT DOCUMENTS 6,217,566 B1 4/2001 Ju et al.
6,508,806 B1 * 1/2003 Hoste .................. A61M 25/005 604/524

(Continued)

FOREIGN PATENT DOCUMENTS

WO 2020018934 A1 1/2020

OTHER PUBLICATIONS

International Preliminary Report on Patentability for International Application No. PCT/US2021/014895, mailed Aug. 4, 2022, 09 Pages.

(Continued)

*Primary Examiner* — William R Carpenter
*Assistant Examiner* — Robert F Allen
(74) *Attorney, Agent, or Firm* — Polsinelli PC

(57) ABSTRACT

The disclosure provides for a variable stiffness catheter. The catheter may include an inner layer forming an inner lumen, a middle layer surrounding the inner layer, and an outer layer surrounding the middle layer. The middle layer may include an annular lumen and a plurality of strings within the annular lumen, and the plurality of strings may be connected to the inner layer. Applying a vacuum and evacuating the annular lumen of the middle layer alters a frictional force between the inner layer and the outer layer and thereby changes the catheter's flexural rigidity.

19 Claims, 3 Drawing Sheets

(52) U.S. Cl.
CPC ..... *A61M 25/0155* (2013.01); *A61M 25/0012* (2013.01); *A61M 2025/0024* (2013.01); *A61M 2025/0025* (2013.01); *A61M 2025/0039* (2013.01); *A61M 2025/004* (2013.01); *A61M 25/0053* (2013.01); *A61M 25/01* (2013.01); *A61M 2025/0175* (2013.01)

(58) Field of Classification Search
CPC ...... A61M 2025/0039; A61M 25/0053; A61M 25/0012; A61M 2025/0024; A61M 25/0054; A61M 25/01; A61M 2025/004; A61M 2025/0175; A61M 25/0026
See application file for complete search history.

(56) References Cited

U.S. PATENT DOCUMENTS

| | | | | |
|---|---|---|---|---|
| 8,125,755 | B2 * | 2/2012 | Garcia | B25J 18/06 361/233 |
| 8,496,648 | B2 * | 7/2013 | Rogers | A61B 17/3421 606/1 |
| 9,155,451 | B2 * | 10/2015 | Smith | A61B 1/0055 |
| 10,123,683 | B2 * | 11/2018 | Smith | A61B 1/31 |
| 10,307,568 | B2 * | 6/2019 | Rogers | A61B 1/0051 |
| 10,835,112 | B2 * | 11/2020 | Smith | A61B 1/0057 |
| 2002/0151823 | A1 * | 10/2002 | Miyata | A61M 25/09 600/585 |
| 2006/0069346 | A1 * | 3/2006 | Smith | A61M 25/005 604/95.05 |
| 2006/0211979 | A1 * | 9/2006 | Smith | A61F 2/0105 604/11 |
| 2007/0060880 | A1 * | 3/2007 | Gregorich | A61M 25/0097 604/95.04 |
| 2012/0179097 | A1 | 7/2012 | Cully | |
| 2012/0277729 | A1 * | 11/2012 | Melsheimer | A61M 25/01 604/525 |
| 2013/0237950 | A1 | 9/2013 | Gianotti et al. | |
| 2013/0245551 | A1 * | 9/2013 | O'Day | A61M 25/0053 604/95.04 |
| 2015/0216589 | A1 * | 8/2015 | Wittenberger | A61M 25/0147 604/95.04 |
| 2017/0151417 | A1 * | 6/2017 | Takemura | A61M 25/09 |
| 2020/0178763 | A1 * | 6/2020 | Tilson | A61B 1/00078 |
| 2025/0090801 | A1 * | 3/2025 | Zayed | A61M 25/0053 |

OTHER PUBLICATIONS

International Search Report and Written Opinion for International Application No. PCT/US2021/014895, mailed Apr. 27, 2021, 10 Pages.

* cited by examiner

VARIABLE STIFFNESS CATHETER AND METHODS THEREOF

CROSS REFERENCE TO RELATED APPLICATIONS

This application is a U.S. national phase application of PCT Application No. PCT/US2021/014895, filed Jan. 25, 2021, which claims priority under 35 USC § 119(e) to U.S. Patent Application Ser. No. 62/965,525, filed on Jan. 24, 2020, the entire contents of which are hereby incorporated by reference.

FIELD

The present disclosure is directed to a temporally variable stiffness catheter and methods of use thereof.

BACKGROUND

Over the last few decades, advancements in visceral peripheral arterial, neurovascular arterial, and venous branch cannulations have evolved with the evolution of available endovascular devices. Currently difficulties exist in highly tortuous and angulated vascular systems. This leads to the need for the use of multiple catheters and sheaths that are advanced into one another to provide staged stiffness and an axial system for advancement of devices to distal target vessels. Current branch vessels of the peripheral vasculature that are challenging to primarily catheterize include but are not limited to the celiac artery, renal artery, superior mesenteric artery/vein, splenic artery/vein, gastroduodenal artery/vein, hepatic artery/vein, tortuous femoral arteries/veins, distal tibial arteries/veins, and branches of the *profunda* femoris artery/vein. Similarly, catheterization of the neurovascular tree can be quite challenging in terms of accessing the internal and external carotid arteries and their intracranial branches, as well as the vertebral arteries.

Currently, surgeons use a coaxial system of catheters to offer navigation and support during surgeries. A floppy intermediate guide catheter is introduced surrounding a guidewire to navigate the vasculature. Once the guide catheter is in place, a larger, stiff sheath is pushed coaxially along the outside to provide support for the system to send a medical device to the brain or peripheral vascular tree. This leads to herniation, which occurs when the stiffer sheath dislodges the floppy guide catheter from its path as it is moved coaxially to cover the guide catheter. Herniation can also occur if no sheath is used for support during intervention—the medical device will cause the guide catheter to herniate into the ascending or descending aortic arch when it passes through the guide catheter. Another problem with current catheters is buckling. Buckling occurs when a medical device kinks the catheter or creates a turn that is too sharp to travel through.

Accordingly, there remains a need for a variable stiffness catheter to be flexible enough to navigate the vasculature from radial, ulnar, femoral, popliteal, carotid, jugular, and pedal access and stiff enough to provide support for medical devices passed through the catheter.

BRIEF SUMMARY

The disclosure provides for a variable stiffness catheter. The variable stiffness catheter may include an inner layer forming an inner lumen, a middle layer forming an annular lumen and surrounding the inner layer, the annular lumen being fluidly connected to a vacuum source, and an outer layer surrounding the middle layer. Applying the vacuum and evacuating the annular lumen of the middle layer alters a frictional resistance or adhesion between the inner layer and the outer layer and thereby changes the catheter's flexural rigidity. The middle layer has a low flexural rigidity or shear resistance when the vacuum is not applied and a high flexural rigidity or shear resistance when the vacuum is applied, and the catheter has a variable stiffness along a length of the catheter between a proximal end and a distal end of the catheter. In some aspects, evacuation of the annular lumen of the middle layer changes the flexural rigidity or adhesion of the middle layer. Evacuation of the annular lumen of the middle layer causes an increase in the frictional resistance or adhesion that enables the inner layer, the middle layer, and the outer layer to flex as if they were a single layer, thereby increasing the flexural rigidity of the inner layer, the middle layer, and the outer layer beyond a sum of their flexural rigidities. There may be variable frictional resistance or adhesion between contacting surfaces of the inner layer and the outer layer on the middle layer. The lower flexural rigidity or shear resistance may be from continuous full microfluidic patency of the annular lumen connecting to the vacuum source and the high shear rigidity of the catheter may be from the friction or adhesion arising when the vacuum source is applied/activated. The catheter may have a variable stiffness on a portion of the length of the catheter. The catheter may have a variable stiffness along a length of the catheter between a proximal end and a distal end of the catheter. The catheter may have a variable stiffness along a portion or more than one portion of the length of the catheter. The location of the portion of the catheter having variable stiffness may be optimized for a specific surgical procedure, including the treatment of a stroke, physiological monitoring, thrombectomy, atherectomy, stenting, ballooning, embolization, ablation, implantation of devices, diagnostic evaluation, PE, arterial/venous thrombus, aneurysm treatment, treating damaged arteries and veins, neurologic disorders to treat stroke, Parkinson's, controlling hemorrhage, and/or dialysis access treatment. The middle layer may include a plurality of strings within the annular lumen. The plurality of strings may be in a spiral formation or linear formation along the length of the inner layer. The plurality of strings may be placed, distributed, or oriented asymmetrically. The catheter may have a variable stiffness from the proximal end to the distal end of the catheter. Additionally, the variable stiffness aspect may be asymmetric (e.g. on side of the catheter) on a portion of a catheter to enable preferential bending or straightening when manipulated. The catheter may have a variable stiffness that is asymmetric or helical along of one portion or more than one portion of the length of the catheter. The structuring may be so as to induce bending of the catheter that augments anchoring, curvature, or torsion of the catheter over a defined region. The anchoring, curvature, or torsion of the catheter may be actuated by release of the vacuum in the middle layer.

In another aspect, the variable stiffness catheter may include an inner layer forming an inner lumen, a middle layer surrounding the inner layer, the middle layer having an annular lumen and a plurality of strings within the annular lumen, and an outer layer surrounding the middle layer. The variable stiffness catheter may be operable to have a low stiffness configuration and a high stiffness configuration upon actuation of a vacuum to the middle layer. The catheter may have a variable stiffness on a portion of the catheter. The location of the portion of the catheter having variable stiffness is optimized for a specific surgical procedure, including the treatment of a stroke, physiological monitoring, thrombectomy, atherectomy, stenting, ballooning, embolization, ablation, implantation of devices, diagnostic evaluation, PE, arterial/venous thrombus, aneurysm treatment, treating damaged arteries and veins, neurologic disorders to treat stroke, Parkinson's, controlling hemorrhage, and/or dialysis access treatment. The inner layer may be relatively non-compliant and the outer layer may be relatively compliant. The plurality of strings are in a spiral formation or linear formation along the length of the inner layer. The plurality of strings may be placed, distributed, or oriented asymmetrically. In some aspects, the inner layer may further comprise a braid on its outer surface. In additional aspects, the outer layer may include a coating. In further aspects, the variable stiffness catheter may further comprise a vacuum source fluidly connected to the annular lumen of the middle layer. The variable stiffness catheter is in the low stiffness configuration when the vacuum source is not actuated and is in the high stiffness configuration when the vacuum source is actuated. The inner layer, the plurality of strings, and the outer layer may be compressed together in the high stiffness configuration. The inner lumen is operable to receive a neurovascular, body vascular, or pulmonary vascular medical device. The variable stiffness catheter may be operable to reduce herniation and buckling in the vasculature when inserted radially.

The disclosure also provides methods of providing transradial interventions. The method may include inserting a variable stiffness catheter through a radial, ulnar, femoral, popliteal, carotid, jugular, or pedal artery of a patient and navigating the variable stiffness catheter through the patient's vasculature when the variable stiffness catheter has a low flexural rigidity or shear resistance. The method may further include fluidly connecting a vacuum source to the annular lumen of the variable stiffness catheter and applying the vacuum to the annular lumen to compress together the inner layer, the plurality of strings, and the outer layer, creating high flexural rigidity or shear resistance. In some aspects, the method may further include inserting a medical device through the inner lumen of the variable stiffness catheter. The medical device may be a neurovascular, body vascular, or pulmonary vascular medical device. The inner layer of the variable stiffness catheter may be relatively non-compliant and the outer layer of the variable stiffness catheter may be relatively compliant. The inner layer of the variable stiffness catheter may further comprise a braid on its outer surface and/or a casing surrounding the outer layer. In some aspects, the variable stiffness catheter may be operable to reduce herniation and buckling in the vasculature when inserted radially.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein.

DETAILED DESCRIPTION

Figure 1:
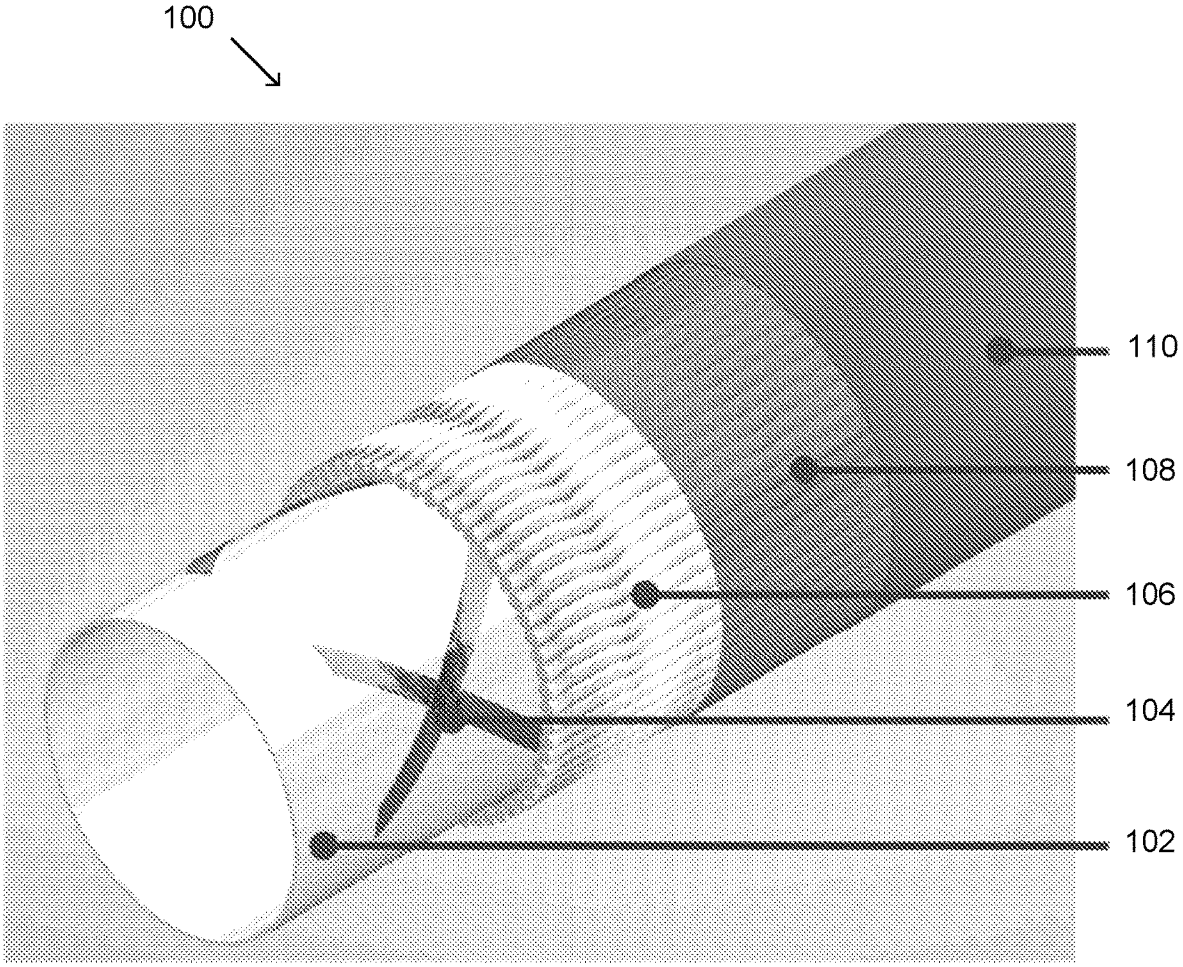
FIG. 1 is an illustration of the variable stiffness catheter, in one example.

The disclosure may be understood by reference to the following detailed description, taken in conjunction with the drawings as described below. It is noted that, for purposes of illustrative clarity, certain elements in various drawings may not be drawn to scale. Several variations of the device are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

Several definitions that apply throughout this disclosure will now be presented. As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

Endovascular catheters must navigate to the target site within a patient, and once at the target site, the catheter (or catheter system) must provide enough support for medical devices such as stents, balloons, thrombectomy devices, intrasaccular aneurysm occlusion devices, coils, and hemodynamic monitoring devices to reach the target site. If an intervention is performed using a compliant catheter system, the catheter(s) are likely incapable of providing adequate support. Stiff, supportive catheters are thus necessary for performing intervention, and they are especially important for delicate, precise surgeries such as those performed by neurovascular surgeons, vascular surgeons, cardiologists, interventional radiologists, and other interventionalists. That being said, increasing a catheter's stiffness, or stability, decreases its ability to successfully navigate through the arterial and venous vasculature.

When a sufficient external force acts on compliant catheters, they may deform by way of kinking, buckling, or herniating. Stiff catheters provide stable platforms to advance medical devices through their lumen, but are difficult to steer due to their increased rigidity.

Disclosed herein is a catheter with temporally variable stiffness. The variable stiffness catheter has a low stiffness configuration and a high stiffness configuration to prevent herniation and buckling in the vasculature but also provide structure for advancing medical devices. Vacuum actuation may be used to alter the inertial properties of the catheter and maximize the change in its flexural rigidity or shear resistance, thus providing variable stiffness between a low stiffness configuration (e.g. a floppy state or non-actuated state) and a high stiffness configuration (e.g. a stiff state or actuated state) on demand. The variable stiffness may allow for the catheter to be used through radial access by being floppy/flexible enough to navigate the vasculature and stiff enough to provide support for medical devices passed through the catheter. In various embodiments, the catheter may be used in transradial neurovascular, body vascular, or pulmonary vascular interventions. For example, the catheter may begin in its low stiffness configuration to navigate the vasculature and reach the brain. Then, the catheter may be actuated by a surgeon with an indeflator, or other negative pressure device or vacuum device found in standard operating suites, to reach the desired change in stiffness to support the medical device. The catheter may be used for endovascular applications, neurovascular applications and non-neurovascular applications. In some non-limiting examples, the catheter may be used for cerebrovascular, pulmonary artery, peripheral vascular applications, or used in other arterial and venous structures that range from 1 mm to 25 mm in diameter.

In an embodiment, the variable stiffness catheter 100 may include a supported inner layer 102, a compliant outer layer 108, and a middle layer 106 of "strings" 105 disposed in an annular lumen 107 between the inner and outer layers, as seen in FIG. 1. In some examples, the catheter may further include a coating 110 surrounding the outer layer 108. The catheter 100 may have a low stiffness configuration and a high stiffness configuration that may be changed based on actuation of a vacuum on the middle layer.

For example, the variable stiffness catheter 100 includes an inner layer 102 forming an inner lumen, a middle layer 106 surrounding the inner layer 102, and an outer layer 108 surrounding the middle layer 106. The middle layer 106 may form an annular lumen. The annular lumen of the middle layer 106 may be fluidly connected to a vacuum source such that the middle layer has a low flexural rigidity or shear resistance when the vacuum is not actuated and a high flexural rigidity or shear resistance when the vacuum is actuated. There may be variable frictional resistance or adhesion between contacting surfaces of the inner layer and the outer layer on the middle layer. Thus, applying the vacuum and evacuating the annular lumen of the middle layer alters the frictional resistance or adhesion between the inner layer and the outer layer and thereby changes the catheter's flexural rigidity. The middle layer has a low flexural rigidity or shear resistance when the vacuum is not applied and a high flexural rigidity or shear resistance when the vacuum is applied. The lower flexural rigidity or shear resistance may be from continuous full microfluidic patency of the region connecting to the vacuum source in the catheter and the high flexural rigidity or shear resistance may be from the friction or adhesion arising when the vacuum source is applied or activated. These aspects may allow the catheter to have a variable stiffness along a length of the catheter between a proximal end and a distal end of the catheter. In some examples, the catheter may have variable stiffness along a portion or segment between its proximal and distal ends, and in other examples, the catheter may have variable stiffness along its entire length from its proximal to distal end.

The inner layer 102 may provide the initial structure of the catheter by forming an inner lumen with a diameter of about 1.5 mm to about 2 mm. In at least one example, the inner lumen may have a diameter of about 1.78 mm. In additional examples the inner layer 102 may form an inner lumen with a diameter of about 0.70 mm to about 0.72 mm. The inner lumen may be operable to receive a neurovascular medical device, including but not limited to embolic agents, coils, balloons, stents, medications, catheters, neuromodulation devices, pressure monitoring, and/or catheter ablation devices. The catheter and/or neurovascular device may be used for the treatment of a stroke, physiological monitoring, thrombectomy, atherectomy, stenting, ballooning, embolization, ablation, implantation of devices, diagnostic evaluation, PE, arterial/venous thrombus, aneurysm treatment, treating damaged arteries and veins, neurologic disorders to treat stroke, Parkinson's, controlling hemorrhage, and/or dialysis access treatment.

The inner layer 102 may reduce friction and support the strings 105 from the middle layer 106. In some examples, the inner layer 102 may be non-compliant or relatively non-compliant. The inner layer may be made of materials including but not limited to nylon, polyether block amide (e.g. Pebax®), PTFE, PU, and other plastic polymers. In some examples, the inner layer 102 is thin and non-deforming when a vacuum is applied to the annular lumen 107. However, as described below, in certain embodiments, the inner layer may be collapsible. Accordingly, the inner layer 102 may also be made from a material including but not limited to latex, polyether block amide (e.g. Pebax®), and/or silicone. The inner layer 102 may have a thickness of about 0.02 mm to about 0.05 mm. In at least one example, the inner layer 102 has a thickness of about 0.036 mm. The inner layer 102 may be supported, for example, with a braid 104 on the outer diameter of the inner layer 102. The braid 104 may be a thin layer that supports the inner layer 102 against buckling. In some examples, the braid 104 may be arranged in a crossing pattern to aid in the support of the inner layer 102, as seen in FIG. 1. The braid 104 may have a thickness of about 0.01 mm to about 0.04 mm. In at least one example, the braid 104 has a thickness of about 0.025 mm. The braid 104 may be made of nitinol in some examples.

The middle layer 106 may include an annular lumen 107 with an array of thin tubes or strings 105 that surround the inner layer 102. The strings 105 may add stiffness and maximize the thickness of the catheter 100 when the catheter is in an actuated state. The strings 105 may extend the longitudinally along the length of the annular lumen 107, and may attach to the proximal and distal ends of the inner layer 102. In some examples, the strings 105 may be in a spiral configuration along the length of the annular lumen 107. In at least one example, the strings 105 may be placed side by side in a linear formation to encase the inner layer 102 with a single sheet of strings 105. In other examples, the strings 105 may be placed, distributed, or oriented asymmetrically. The middle layer 106 may include between about 40 strings and about 170 strings, depending on the diameter of the strings. In various examples, the maximum number of strings may be up to 47 strings, up to 71 strings, up to 80 strings, up to 88 strings, up to 150 strings, or up to 163 strings. In at least one example, the middle layer 106 may include about 60 strings. The distance between each string 105 may range from about 0 mm to about 0.02 mm. In some examples, the strings 105 may be nitinol wires or synthetic threads. Non-limiting examples of threads include metallic threads, monofilament threads, and fibers. The strings 105 may have a radius of about 0.05 mm to about 0.2 mm. In various examples, the strings 105 may have a radius of about 0.056 mm, 0.083 mm, 0.108 mm, or 0.167. In at least one example, the strings 105 have a radius of about 0.0825 mm. The density and diameter of the strings 105 may affect the rigidity of the catheter 100.

The outer layer 108 may be a compliant or relatively complaint layer that surrounds the middle layer 106 and inner layer 102 of the catheter 100. In some examples, the outer layer 108 is thin and tear-resistant, such that it can withstand the vacuum/suction applied to the middle layer. When the catheter 100 is actuated, air within the annular lumen 107 is evacuated, and the outer layer 108 collapses down to compress the inner layer 102 and strings 105 as one unified body. Alternatively, the collapsible layer may comprise the inner (as opposed to the outer) layer of the catheter. Accordingly, in an embodiment, when the catheter 100 is actuated, air within the annular lumen 107 is evacuated, and the inner layer 102 collapses outward to compress the strings 105 and the outer layer 108 as one unified body. In this alternative embodiment, the outer layer 108 forms a non-compliant structure. The activated state is mathematically stiffer than the original state. The material used to form the outer layer 108 (and the inner layer 102 described above) will depend on whether or not the layer is intended to be collapsible. In some examples, the outer layer 108 may be made of a material including but not limited to latex, polyether block amide (e.g. Pebax®), and/or silicone. Alternatively, if the outer layer is non-compliant, it may be made from materials such as nylon, polyether block amide (e.g. Pebax®), PTFE, PU, and other plastic polymers. In some examples, the outer layer 108 is thin and non-deforming when a vacuum is applied to the annular lumen 107. In various embodiments, the outer layer 108 is opaque. The outer layer 108 may have a thickness of about 0.01 mm to about 0.03 mm. In at least one example, the outer layer 108 has a thickness of about 0.0175 mm. The outer layer 108 may be further surrounded by a coating 110 in some examples. The coating may be a hydrophilic coating. The coating 110 may have a thickness of about 0.01 mm to about 0.03 mm. In at least one example, the coating 110 has a thickness of about 0.0175 mm.

Figure 2:
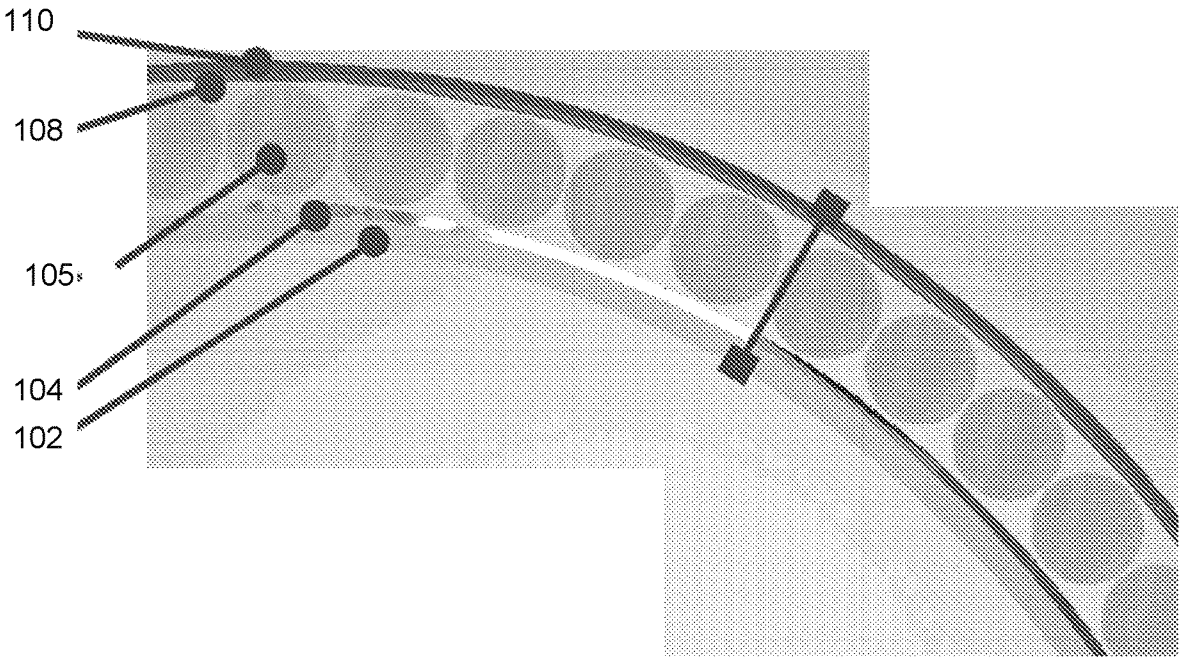
FIG. 2 shows a portion of a cross-section of the variable stiffness catheter, in one example.

FIG. 2 shows a cross section of the layers of the catheter 100, in one example. The catheter 100 may have an inner diameter ranging from about 1.5 mm to about 7 mm. In various examples, the catheter 100 has an inner diameter of about 1.778 mm, 2.235 mm, 5.333 mm, 5.667 mm, 6.0 mm, 6.333 mm, or 6.667 mm. In at least one example, the catheter 100 has an inner diameter of about 1.778 mm. Alternatively, the catheter 100 may have an inner diameter ranging from about 0.70 mm to 0.72 mm. The catheter 100 may have an outer diameter ranging from about 1.6 mm to about 8 mm in the actuated state. In various examples, the catheter 100 has an outer diameter of about 2.0 mm, 2.667 mm, 6.0 mm, 6.667 mm, or 7.333 mm. In at least one example, the catheter 100 has an outer diameter of about 2.1 mm. The catheter 100 ranges in size from 5 French to 26 French. In various examples, the catheter 100 may have a size of about 5 French, 6 French, 7 French, 8 French, 9 French, 10 French, 11 French, 12 French, 13 French, 14 French, 15 French, 16 French, 17 French, 18 French, 19 French, 20 French, 21 French, 22 French, 23 French, 24 French, 25 French, or 26 French. For example, the catheter 100 may have a size of 6 French or 20 French. When the layers of the catheter 100 are compressed, the catheter 100 may have a thickness of about 0.1 mm to about 0.2 mm. In at least one example, the catheter 100 has a thickness of about 0.127 mm to 0.161 mm. The catheter 100 thickness may include the thickness of the inner layer 102, braid 104, strings 105, outer layer 108, and/or coating 110, as seen in FIG. 2.

The catheter may include a connector at its proximal end for connecting a vacuum source. The vacuum source may be fluidly connected to the annular lumen of the middle layer. In some examples, the vacuum source may be an indeflator or a syringe. The catheter may include an atraumatic distal end to prevent luminal dissection.

Figure 3A:
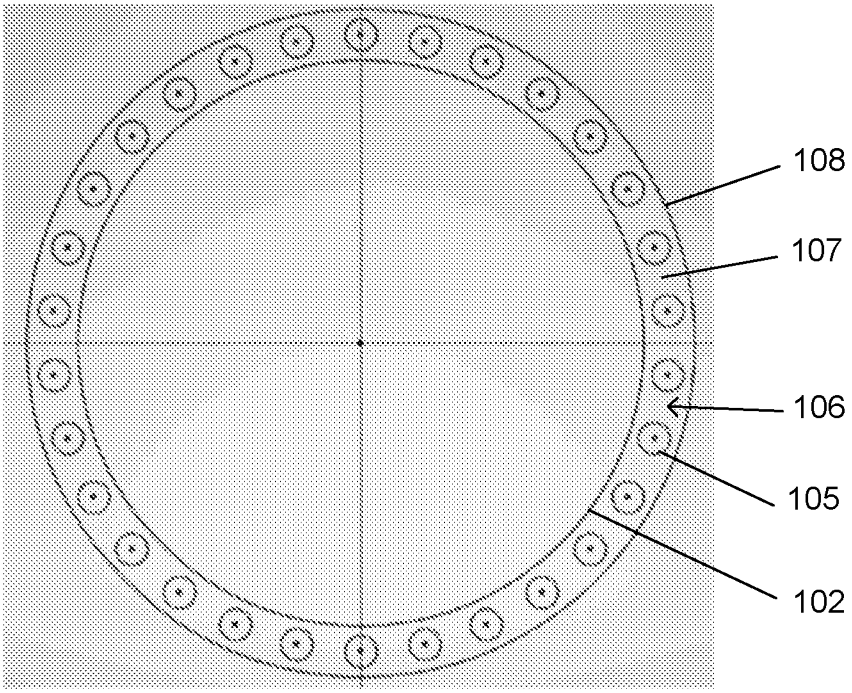
FIG. 3A shows a cross-section of the variable stiffness catheter in a low stiffness configuration, in one example.
Figure 3B:
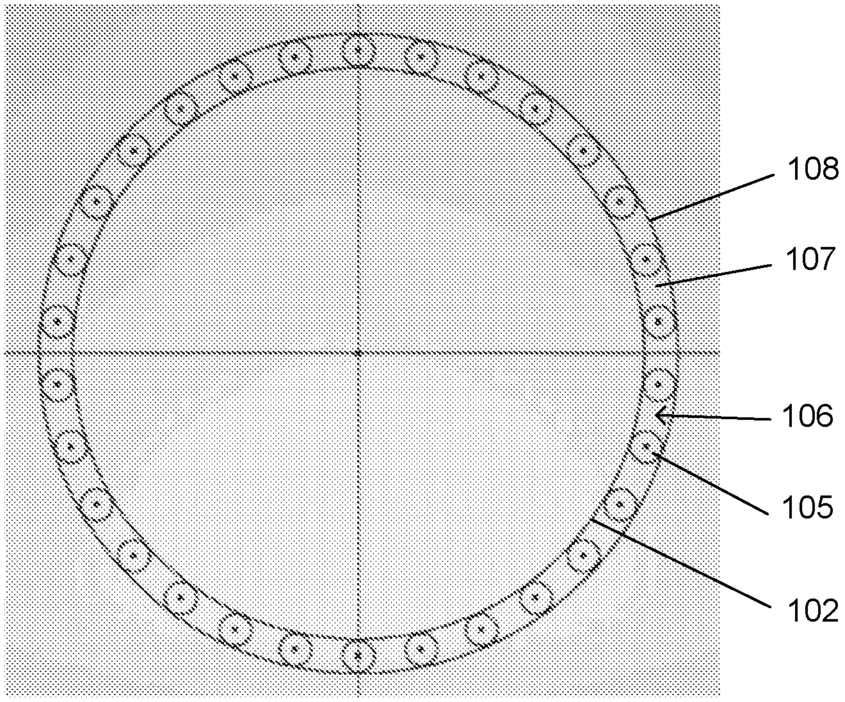
FIG. 3B shows a cross-section of the variable stiffness catheter in a high stiffness configuration, in one example.

Evacuation of the annular lumen 107 of the middle layer changes the flexural rigidity or shear resistance of the middle layer. This may enable the catheter 100 to assume two different stiffness configurations: a low stiffness configuration (vacuum not applied/actuated) and a high stiffness configuration (vacuum applied/actuated). FIG. 3A shows an example cross section of the catheter in the low stiffness or low flexural rigidity configuration. In the low stiffness or low flexural rigidity configuration, the annular lumen 107 defined between the inner and outer layers is maintained at approximately atmospheric pressure, enabling the adjacent surfaces of the inner and outer layers, as well as the plurality of strings, to slide freely relative to one another, such that each of these three elements functions essentially independently with respect to structural stiffness of the catheter. FIG. 3B shows an example cross section of the catheter in the high stiffness or high flexural rigidity configuration. In the high stiffness or high flexural rigidity configuration, the annular lumen is evacuated under negative (vacuum) pressure, causing the collapse of the annular lumen and accompanying close contact of the adjacent surfaces of the inner and outer layers and strings. In the high stiffness or high flexural rigidity configuration, the inner and outer layers and strings function essentially as a single composite structure with significantly enhanced stiffness. For example, evacuation of the annular lumen of the middle layer causes an increase in the frictional resistance or adhesion that enables the inner layer, the middle layer, and the outer layer to flex as if they were a single layer, thereby increasing the flexural rigidity or shear resistance of the inner layer, the middle layer, and the outer layer beyond a sum of their flexural rigidities. The transition between the low and high stiffness configurations is controlled by the application and removal of a vacuum source from the annular lumen.

The catheter may have a flexural rigidity of about 1.4 $Nm^2$ to about 6 $Nm^2$ when in the low stiffness configuration. For example, the catheter may have a flexural rigidity of about 1.4 $Nm^2$ to about 2 $Nm^2$, about 2 $Nm^2$ to about 4 $Nm^2$, and about 4 $Nm^2$ to about 6 $Nm^2$ when in the low stiffness configuration. The catheter may have a flexural rigidity of about 6 $Nm^2$ to about 15 $Nm^2$ when in the high stiffness configuration. For example, the catheter may have a flexural rigidity of about 6 $Nm^2$ to about 8 $Nm^2$, about 8 $Nm^2$ to about 10 $Nm^2$, and about 10 $Nm^2$ to about 15 $Nm^2$ when in the high stiffness configuration.

The catheter 100 may have a length from about 10 cm to about 100 cm, from about 10 cm to about 90 cm, from about 10 cm to about 80 cm, from about 10 cm to about 70 cm, from about 10 cm to about 60 cm, from about 10 cm to about 50 cm, from about 10 cm to about 40 cm, from about 10 cm to about 30 cm, or from about 10 cm to about 20 cm. The catheter 100 may have a length from about 20 cm to about 100 cm, from about 20 cm to about 90 cm, from about 20 cm to about 80 cm, from about 20 cm to about 70 cm, from about 20 cm to about 60 cm, from about 20 cm to about 50 cm, from about 20 cm to about 40 cm, or from about 20 cm to about 30 cm. The catheter 100 may have a length from about 30 cm to about 100 cm, from about 30 cm to about 90 cm, from about 30 cm to about 80 cm, from about 30 cm to about 70 cm, from about 30 cm to about 60 cm, from about 30 cm to about 50 cm, from about 30 cm to about 40 cm. The catheter 100 can have a length of from about 40 cm to about 100 cm, from about 40 cm to about 90 cm, from about 40 cm to about 80 cm, from about 40 cm to about 70 cm, from about 40 cm to about 60 cm, or from about 40 cm to about 50 cm. The catheter 100 can have a length of from about 50 cm to about 100 cm, from about 50 cm to about 90 cm, from about 50 cm to about 80 cm, from about 50 cm to about 70 cm, from about 50 cm to about 60 cm. The catheter 100 can have a length of from about 60 cm to about 100 cm, from about 60 cm to about 90 cm, from about 60 cm to about 80 cm, or from about 60 cm to about 70 cm. The catheter 100 can have a length of from about 70 cm to about 100 cm, from about 70 cm to about 90 cm, or from about 70 cm to about 80 cm. Alternatively, the catheter 100 can have a length of from about 80 cm to about 100 cm or from about 80 cm to about 90 cm. Alternatively, the catheter 100 can have a length of from about 90 cm to about 100 cm. For example, the catheter can have a length of about 30, 60, or 100 cm.

In some embodiments, the catheter may have variable stiffness capabilities along a length of the catheter between its proximal end and its distal end. For example, there may be variable frictional resistance or adhesion between contacting surfaces of the inner layer and the outer layer on the middle layer. For example, only a portion or segment or more than one portion of the length of the catheter may have the variable stiffness capabilities, and the remaining portions of the catheter may remain compliant or stiff, depending on the use and/or size of the catheter. In some examples, the location of the portion or segment of the catheter having variable stiffness is optimized for a specific surgical procedure, including but not limited to the treatment of a stroke, physiological monitoring, thrombectomy, atherectomy, stenting, ballooning, embolization, ablation, implantation of devices, diagnostic evaluation, PE, arterial/venous thrombus, aneurysm treatment, treating damaged arteries and veins, neurologic disorders to treat stroke, Parkinson's, controlling hemorrhage, and/or dialysis access treatment. This segment may be at the distal catheter, the mid catheter segment, or the proximal segment of the catheter. There may also be more than one segment of the catheter with rigidity actuation.

In another embodiment, the catheter may have a proximal end with variable stiffness capabilities, while the distal end may be compliant. In some examples, the distal most 5 to 10 cm of the catheter may be compliant without variable stiffness capabilities. In this example, the distal end of the catheter is more flexible than the proximal end, but may still overcome the problems of herniation and buckling. In other embodiments, the length of the catheter from its proximal end to its distal end may have variable stiffness. In still other embodiments, the middle third of the catheter may have variable stiffness.

In an embodiment, the catheter may have pre-formed segments tailored for known areas or arterial angulation or tortuosity. In some embodiments, the catheter may have pre-formed segments to accommodate the aortic arch, variants of the aortic arch and origins of the vertebral and carotid arteries, right atrium, abdominal aorta, iliofemoral artery/vein segments, and upper and lower extremity arterial/venous anatomy. Flexural rigidity actuation may serve to impact the rigidity of the pre-formed segment of the catheter, or segments flanking the pre-formed segment of the catheter.

In additional embodiments, the variable stiffness may be asymmetric or helical along of one portion or more than one portion of the length of the catheter. For example, the variable stiffness may be asymmetric (e.g. on a side of the catheter) on a portion of a catheter to enable preferential bending or straightening when manipulated. The structure of the asymmetric variable stiffness be operable to induce bending of the catheter that augments anchoring, curvature, or torsion of the catheter over a defined region. The anchoring, curvature, or torsion may then be actuated by release of the vacuum in the middle layer. The asymmetric variable stiffness on a side of the catheter may allow for more efficient navigation or anchoring of a catheter for a pre-defined anatomic configuration once the catheter has arrived at that location. The asymmetric stiffness may be range from 1 to 99% of the circumference of the catheter. In at least one example, the asymmetric stiffness may occupy 50% of the circumference of catheter.

EXAMPLES

Example 1

To quantify the change in stiffness, beam theory, which treats the catheter body as a beam subject to an applied moment (rotational force) was used. From the Euler-Bernoulli equation describing beam theory, the flexural rigidity (EI terms) mathematically describes the stiffness of a material, as seen in Eqn. 1

$$M = EI / \rho \qquad \text{Eqn. 1}$$

where M is the moment, E is the elastic modulus, I is the area moment of inertia for the beam cross section, and $\rho$ is the radius of curvature.

The catheter controls the flexural rigidity by changing the moment of inertia (I)—the geometric design of the cross section—and optimizing the elastic modulus (E)—the inherent property of a material that describes its resistance to deformation. The catheter has two distinct states that are characterized by their moments of inertia in the low stiffness configuration and the high stiffness configuration. In the low stiffness configuration, before the vacuum is actuated, the inner layer, middle layer, and outer layer act independently, so the catheter has a low moment of inertia. In the high stiffness configuration, once the vacuum is actuated, all three layers act as one single layer, as if they were glued together. By pairing this change in inertial properties with the most effective materials, the flexural rigidity or shear resistance can be optimized to change by a factor of eight.

Using the methods and theory described above, the flexural rigidity of two different prototypes of the catheters described herein were determined for a 9 Fr alpha prototype and a 6 Fr alpha prototype.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A variable stiffness catheter comprising:

an inner layer forming an inner lumen;

a middle layer forming an annular lumen and surrounding the inner layer, the annular lumen of the middle layer being fluidly connected to a vacuum source, the annular lumen comprising a plurality of strings in a single sheet along at least a portion of a length of the inner layer, wherein the plurality of strings are non-crossing; and an outer layer surrounding the middle layer, wherein applying the vacuum and evacuating the annular lumen of the middle layer alters a frictional resistance or adhesion between the inner layer and the outer layer and thereby increases the catheter's flexural rigidity, and wherein releasing the vacuum decreases the catheter's flexural rigidity.

2. The variable stiffness catheter of claim 1, wherein the middle layer has a low flexural rigidity or shear resistance when the vacuum is not applied and a high flexural rigidity or shear resistance when the vacuum is applied.

3. The variable stiffness catheter of claim 2, wherein the low flexural rigidity or shear resistance of the catheter is from continuous full microfluidic patency of the annular lumen connecting to the vacuum source and the high flexural rigidity or shear resistance of the catheter is from the frictional resistance or adhesion arising when the vacuum source is applied.

4. The variable stiffness catheter of claim 1, wherein evacuation of the annular lumen of the middle layer changes the flexural rigidity or adhesion of the middle layer.

5. The variable stiffness catheter of claim 4, wherein evacuation of the annular lumen of the middle layer causes an increase in the frictional resistance or adhesion that enables the inner layer, the middle layer, and the outer layer to flex as if they were a single layer, thereby increasing the flexural rigidity of the inner layer, the middle layer, and the outer layer beyond a sum of their flexural rigidities.

6. The variable stiffness catheter of claim 1, wherein there is variable frictional resistance or adhesion between contacting surfaces of the inner layer and the outer layer on the middle layer.

7. The variable stiffness catheter of claim 1, wherein the catheter has a variable stiffness along a length of the catheter between a proximal end and a distal end of the catheter.

8. The variable stiffness catheter of claim 7, wherein the catheter has a variable stiffness along a portion or more than one portion of the length of the catheter.

9. The variable stiffness catheter of claim 8, wherein a location of the portion of the catheter having variable stiffness is optimized for a specific surgical procedure.

10. The variable stiffness catheter of claim 7, wherein the variable stiffness is along an asymmetric side of one portion or more than one portion of the length of the catheter.

11. The variable stiffness catheter of claim 1, wherein the plurality of strings are in a spiral formation or linear formation along a length of the inner layer.

12. The variable stiffness catheter of claim 1, wherein the inner layer is relatively non-compliant and the outer layer of the catheter is relatively compliant.

13. The variable stiffness catheter of claim 1, wherein the inner layer further comprises a braid on its outer surface.

14. The variable stiffness catheter of claim 1, further comprising a casing surrounding the outer layer.

15. A method of providing transradial interventions, the method comprising:

inserting the variable stiffness catheter of claim 1 through a radial artery of a patient; and navigating the variable stiffness catheter through the patient's vasculature, wherein the variable stiffness catheter has a low flexural rigidity.

16. The method of claim 15, further comprising:

fluidly connecting a vacuum source to the annular lumen; and applying the vacuum to the annular lumen to compress together the inner layer, and the outer layer, creating high flexural rigidity.

17. The method of claim 16, further comprising:

inserting a medical device through the inner lumen of the variable stiffness catheter.

18. The method of claim 17, wherein the medical device is a neurovascular, body vascular, or pulmonary vascular medical device.

19. The method of claim 15, wherein the variable stiffness catheter is operable to reduce herniation and buckling in the vasculature when inserted radially.

* * * * *